(12) United States Patent
Sadat

(10) Patent No.: US 10,806,493 B2
(45) Date of Patent: Oct. 20, 2020

(54) SADAT FIXATION DEVICE AND METHOD

(71) Applicant: Safiullah Sadat, Burnaby (CA)

(72) Inventor: Safiullah Sadat, Burnaby (CA)

( * ) Notice: Subject to any disclaimer, the term of this patent is extended or adjusted under 35 U.S.C. 154(b) by 137 days.

(21) Appl. No.: 15/823,501

(22) Filed: Nov. 27, 2017

(65) Prior Publication Data

US 2019/0159809 A1    May 30, 2019

(51) Int. Cl.
*A61B 17/64* (2006.01)
*A61B 17/66* (2006.01)

(52) U.S. Cl.
CPC .......... *A61B 17/6441* (2013.01); *A61B 17/66* (2013.01)

(58) Field of Classification Search
CPC ... A61B 17/6441; A61B 17/645; A61B 17/64; A61B 17/62; A61B 17/66; A61B 17/6416; A61B 17/6425; A61B 17/6433; A61B 17/6458; A61B 17/6466; A61B 17/6475; A61B 17/6483

See application file for complete search history.

(56) References Cited

U.S. PATENT DOCUMENTS

| | | | | |
|---|---|---|---|---|
| 2,055,024 | A | * 9/1936 | Bittner, Jr. | A61B 17/62 606/56 |
| 3,727,610 | A | * 4/1973 | Riniker | A61B 17/6441 606/56 |
| 4,365,624 | A | * 12/1982 | Jaquet | A61B 17/62 606/56 |
| 4,624,249 | A | * 11/1986 | Alvarez Cambras | A61B 17/6441 606/54 |
| 5,431,651 | A | 7/1995 | Goble | |
| 5,976,125 | A | 11/1999 | Graham | |
| 6,019,762 | A | 2/2000 | Cole | |
| 8,518,039 | B2 | 8/2013 | Mirza et al. | |
| 9,597,130 | B2 | 3/2017 | Pappalardo et al. | |
| 2013/0110110 | A1 | 5/2013 | Waisman | |
| 2013/0245699 | A1 | 9/2013 | Orbay et al. | |
| 2013/0325007 | A1 | 12/2013 | Beyar et al. | |
| 2016/0338746 | A1 | 11/2016 | Scruggs et al. | |

* cited by examiner

*Primary Examiner* — Julianna N Harvey
(74) *Attorney, Agent, or Firm* — Acumen Intellectual Property; Michael C. Balaguy

(57) ABSTRACT

An external bone fixator apparatus for use in orthopedic surgery and treatments is disclosed herein. The present application relates generally to orthopedics. More specifically, the present application relates to apparatus and methods for the repair of fractures or deformities in long bones. Devices of the disclosed system enable fixation of bone fractures during reduction and other orthopedic procedures. These fixation devices may include an adjustable fixation frame having external fixation elements adapted to position Kirschner wires (K-wires) engaging the bone segments of the fracture.

11 Claims, 9 Drawing Sheets

SADAT FIXATION DEVICE AND METHOD

BACKGROUND OF THE INVENTION

1. Field of the Invention

The following includes information that may be useful in understanding the present disclosure. It is not an admission that any of the information provided herein is prior art nor material to the presently described or claimed inventions, nor that any publication or document that is specifically or implicitly referenced is prior art.

The present invention relates generally to the field of external orthopedic fixation means and more specifically relates to bilateral orthopedic fixators, i.e. with both ends of pins or wires clamped.

2. Description of Related Art

Open fractures of the tibia is one of the most common serious injuries sustained by individuals in war and conflict regions around the world. The number of fractures occurring in such conflict zones is predicted to double in the next few years. The annual number of infected open fractures due to gunshots, mine explosions, and other kinds of accidents are also increasing in many regions of the world, especially war-torn countries like Afghanistan, Iraq, and Syria. In advanced countries, traffic accidents are a major cause of fractures. External bone fixation devices are used to stabilize bone segments and to facilitate the healing of bones at a bone-repair site. Such bone-repair sites may contain a bone injury or deformity of the bone structure. Many of these fractures involve the long bones of the extremities including the femur, tibia, fibula, humerus, radius, and ulna. Fractures to these bones can be particularly painful, difficult to heal, and may require to use of specialized external fixation devices that are scarce or unavailable in the countries where treatment is being provided. The lack of critical treatment resources often produces negative outcomes, which must be corrected by subsequent surgeries and extended treatment. Clearly, new and effective bone fixation devices, which have more benefits than previous fixation devices are needed in the field of orthopedics. In particular, new bone fixation devices that are lighter in weight, provide increased comfort to patients, reduce the duration of recovery, provide increased versatility in treatment options, and are available to medical practitioners at a lower cost would benefit many.

Attempts have been made to overcome the above-noted deficiencies in the existing art. By way of example, U.S. Pat. No. 5,976,125 to Graham relates to an external distractor/fixator for the management of fractures and dislocations of interphalangeal joints. The described external distractor/fixator for the management of fractures and dislocations of interphalangeal joints includes external fixation apparatus for reduction and distraction of a joint injury such as fracture or dislocation of the proximal and distal bones of a joint from a location external to the soft tissue of a patient. The device including a proximal fixator, a distal fixator, a proximal wire inserted through the proximal fixator and into a proximal bone, a distal wire inserted through the distal fixator and into a distal bone, and an adjustable distraction mechanism connecting said proximal and distal fixators. This device is significantly less versatile than the Sadat fixation device disclosed herein.

BRIEF SUMMARY OF THE INVENTION

In view of the foregoing disadvantages inherent in the known external orthopedic fixation means art, the present disclosure provides a novel external fixation device and method. The general purpose of the present disclosure, which will be described subsequently in greater detail, relates generally to orthopedics. More specifically, the present application relates to apparatus and methods for the repair of fractures or deformities in long bones. Devices of the disclosed system enable fixation of bone fractures during reduction and other orthopedic procedures. These fixation devices may include an adjustable fixation frame having external fixation elements adapted to position bone-fixation wires engaging the bone segments of the fracture. In particular, such bone-fixation wires are Kirschner-type wires (also referred to as K-wires).

An external bone fixator apparatus for use in orthopedic surgery and treatments is disclosed herein. The an external bone fixator apparatus for use in orthopedic surgery and treatments includes a plurality of arch-shaped support members, each the arch-shaped support member may include a first arm may have a first distal end thereof, a first wire retainer joined with the first distal end, the first wire-retainer configured to firmly retain a first set of bone-fixation wires usable to position a bone part, a second arm pivotally joined to the first arm, the second arm may have a second distal end thereof, a second wire retainer joined with the second distal end, the second wire-retainer configured to firmly retain a second set of bone-fixation wires, the second wire-retainer structured and arranged to enable bone-fixation wires of the second set to include at least one bone-fixation wire of the first set, and a distance-of-separation adjuster configured to enable user-selected adjustments to a separation distance between the first wire retainer and the second wire retainer of a respective the arch-shaped support member; and a plurality of strut-rod assemblies configured to rigidly connect adjacent the arch-shaped support members together to define a fixator frame, each the strut-rod assembly including axially-extending rod members configured to extend between the arch-shaped support members, and a positional adjuster configured to adjust relative geometrical positions of such adjacent the arch-shaped support members.

A method of using an external bone fixator apparatus for use in orthopedic surgery and treatments is also disclosed herein. The method of using an external bone fixator apparatus for use in orthopedic surgery and treatments may comprise the steps of: providing at least two arch-shaped support members, each arch-shaped support member may include a first arm may have a first distal end thereof, a first wire retainer joined with the first distal end, the first wire-retainer configured to firmly retain a first set of bone-fixation wires usable to position a bone part, a second arm pivotally joined to the first arm, the second arm may have a second distal end thereof, a second wire retainer joined with the second distal end, the second wire-retainer configured to firmly retain a second set of bone-fixation wires, the second wire-retainer structured and arranged to enable bone-fixation wires of the second set to include at least one bone-fixation wire of the first set, and a distance-of-separation adjuster configured to enable user-selected adjustments to a separation distance between the first wire retainer and the second wire retainer of a respective arch-shaped support member; providing a plurality of strut-rod assemblies configured to rigidly connect adjacent the arch-shaped support members together to define a fixator frame, each strut-rod assembly including axially-extending rod members configured to extend between the arch-shaped support members, and a positional adjuster configured to adjust relative geometrical positions of the adjacent arch-shaped support members; determining a distance of separation between the first wire retainer and the second wire retainer of each arch-shaped support member required to accommodate a body portion containing the bone part; adjusting the first wire retainer and the second wire retainer of each arch-shaped support member to the required distance of separation; locating the arch-shaped support members adjacent the bone parts of a fracture such that a plane extending between the first wire retainer and the second wire retainer of each arch-shaped support member passes through a respective bone part of the fracture; positioning the bone parts of the fracture by engaging the bone-fixation wires within the first wire retainers, the second wire retainers and the respective bone parts.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an external fixation device and method, constructed and operative according to the teachings of the present disclosure.

The various embodiments of the present invention will hereinafter be described in conjunction with the appended drawings, wherein like designations denote like elements.

DETAILED DESCRIPTION

Figure 1:
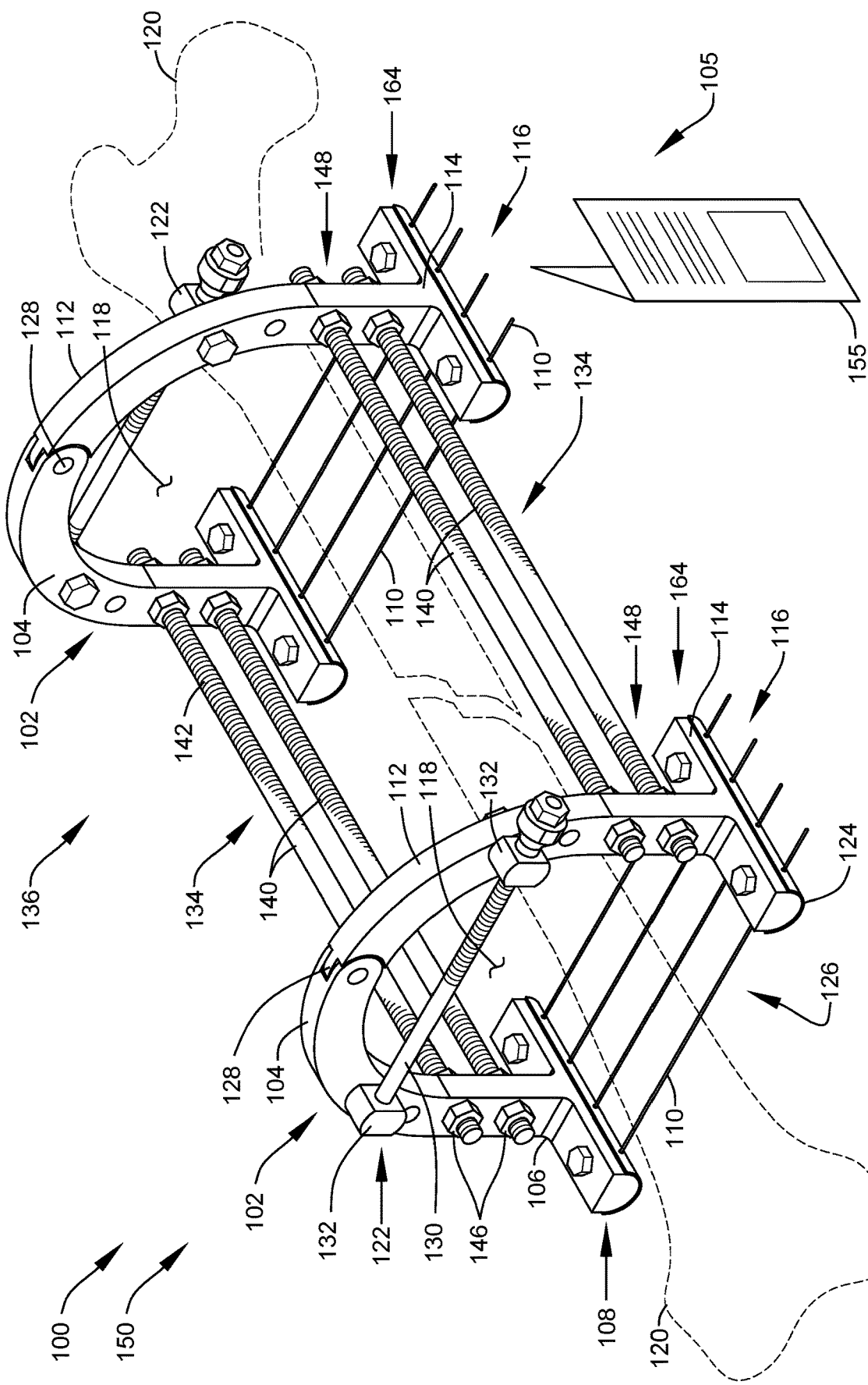
FIG. 1 shows a front perspective view of an external bone fixator apparatus for use in orthopedic surgery and treatments during an 'in-use' condition, according to an embodiment of the disclosure.

As discussed above, embodiments of the present disclosure relate to an external orthopedic fixation means and more particularly to an external fixation device and method as used to improve bilateral orthopedic fixators, i.e. with both ends of pins or wires clamped.

Generally, the medical, mechanical, and multifunctional devices of the disclosed system provide improved fixation of the skeletal system. More specifically, apparatus of the disclosed system provides percutaneous cross or straight threaded K-wire fixation and a non-bridging external fixation for the setting and corrective treatment of pathologies of the skeletal system, especially external fixations used to treat infected open and close fractures of long bones due to gun shot, mine explosions, and other accidents resulting in significant bone injuries.

The presently-disclosed fixation devices are particularly useful in repair tibial-shaft fractures occurring within the length of the bone. In addition, the devices may be used to reduce and stabilize infected fractures and to promote proper healing and recovery of traumatic fractures to prevent pseudoarthrosis within the fracture site. It is therefore an object of the present invention to provide fixation, of the tibia in open and closed infected fractures and in the prevention and treatment of pseudoarthrosis. A principal use of this device is to fix a fracture area by providing a rigid external fixation frame. The external fixation frame of the presently-disclosed system includes a set of articulated arch-shaped support members having a set of opposing arms disposed with respect to a plurality of Kirschner wires (K-wires) extending between the arms. The K-wires used in conjunction with this system may include a centrally-threaded portion to provide firm mechanical engagement with the bone structure. This unusual wire configuration creates a resister fixation in the fracture area and assists in controlling lateral movement of the bone during reduction.

Each articulated arch-shaped support member comprises a pair of opposing arms including a right-half arm section and left-half arm section joined at a pivot. Each arm section defines a generally circular sector having a proximal end-portion containing the pivot and a distal end-portion containing a wire-clamping element adapted engage and firmly lock the K-wires in operable positions extending outwardly from the arch-shaped support members. The angular relationship between these two coupled arm sections may be adjusted by a threaded adjustment rod connecting the half portions at mechanical joints. More specifically, the right-half arm section and left-half arm section each include a rod-receiving block having a threaded bore designed to receive the threaded rod. In this arrangement, the arc formed by the arm sections may be modified by rotation of the threaded rod engaged within the rod-receiving blocks. Thus, a space (separation distance) between the opposing clamping elements of the half-circular support members may be extended and retracted by rotational manipulation of the threaded rod. The arch-shaped support members are joined together in a spaced-apart relationship by a plurality of strut-rod assemblies. These strut-rod assemblies include axially-extending rod members extending between and engaging the arch-shaped support members. The strut-rod assemblies may include one or more positional adjusters configured to adjust the relative geometrical positions of adjacent arch-shaped support members.

In one embodiment of the system, pairs of axially-extending rod members extend between and engage the right and left arms of the arch-shaped support members. During use, the pairs of axially-extending rod members may be located generally bilaterally of the fracture area. The positional adjusters enable adjustments to a distance of separation between the adjacent arch-shaped support members. During treatment of an extremity (e.g., an arm or leg), the open region located within the arch-shaped support members may be placed over the extremity such that the fracture falls generally between the arch-shaped support members. In this position, the axially-extending rod members may be located at medial and lateral positions about the extremity. Fixation of pseudoarthrosis fractures of the tibial shaft may be treated by securing K-wires to the bone segments located on each side of the fracture, followed by adjustment of the distance of separation between the adjacent arch-shaped support members to produce strong axial compression of the fracture via applications of force through the K-wires. Distraction and retraction/compression features may be incorporated into the fixation device and may be used to gradually adjust the relative orientation and spacing of the portions of the bone on opposite sides of a bone-repair site. This external fixation device may comprise one or more rigid and durable materials suitable for medical applications. These materials may include platinum, aluminum, steel, plastic, and fiber-reinforced fiber composites. In general, only K-wire constructed of platinum.

Technical Terms and Methodology

A. Compression: Reducing fractures by controlled application of compression is a primary capability of the apparatus. Compression along the long axis of the bone is accomplished by reducing the distance between the arch-shaped support members engaging the proximal and distal bone segments of the fracture. The axial adjustment is accomplished by manipulating the strut-rod assemblies joining the arch-shaped support members. The adjustment may be performed by a trained medical practitioner. In the absence of a medical practitioner, the patient may perform the manipulation by themselves, after receiving instructions on the procedure.

B. Distraction: Distraction to separate or lengthen the bone is another important capability of apparatus. Distraction is accomplished by increasing the distance between the arch-shaped support members and K-wires engaging the proximal and distal bone segments of the bone. As with compression, the adjustment producing distraction is easily accomplished by manipulating the strut-rod assemblies joining the arch-shaped support members. Distraction may be used in correction of skeletal deformities, for example, if an abnormality of bone geometry occurs after fixation of the fracture or the fractured pieces located opposite each other. The adjustment may be performed by a trained medical practitioner or by the patient after receiving instructions on proper implementation of the procedure.

C. Flexion: Flexion is another important capability of the apparatus. Flexion adjustments are associated with a reduction in the distance between the distal ends of the two opposing arm sections forming the arch-shaped support members. As noted above, manipulating the threaded adjustment rod joining the arm sections adjusts the angular positions of the arm sections about the pivot and distance between the K-wire clamping elements. By way of example, this adjustment may be used in fixation of a tibia fracture where the space between the K-wire clamping elements of the distal the arch-shaped support member may be less than that of the proximal the arch-shaped support member. This arrangement accommodates the generally tapering outer conformation of the lower leg wherein the distal structures of the lower leg are smaller than the proximal structures at the gastrocnemius muscle.

D. Retraction: Retraction is the opposing adjustment to flexion and is another useful capability of the apparatus. Retraction adjustments are associated with an increase in the separation distance and open area volume between the distal ends of the two opposing arm sections of the arch-shaped support members. As noted above, manipulating the threaded adjustment rod joining the arm sections adjusts the angular positions of the arm sections about the pivot and separation distance between the K-wire clamping elements. Another important benefit of retraction is the tensioning of the K-wires extending between opposing clamping elements of the arch-shaped support members. High K-wire tension is associated with improved fixation stability and resistance to detrimental bone movement at the fracture site, particularly when threaded K-wires are used.

E. Creation of Rotational movement: The creation of rotational movement is one of the main characteristics of the apparatus. Each connection point of upper axially-extending rod members are capable of about two centimeters of rotational movement. Thus, the distal and proximal arch-shaped support members can achieve a relative rotational movement of up to about four centimeters in opposing directions. This rotation produces corresponding rotations of the K-wires fixed within the distal and proximal arch-shaped support members. The geometric relationships between the elements of the fixation frame may be firmly fixed after adjustment. These adjustment operations also have major role in the selection of the areas and volumes of space within the arch-shaped support members. Flexion in the area may also be created. By way of example, fixation of a tibia fracture may require a smaller open area within the distal arch-shaped support member as the space required to accommodate the distal portion of the leg is less approaching the ankle. Correction of angle in fractured area: Angular deviations within the fracture area often occur and may cause mal-unions and other abnormalities in bone alignment if not properly treated. Such angulations can be corrected by fixation of the bone in opposition to the angle of the fractured area using the disclosed fixation device. In this manner, the practitioner can favorably manage the misalignment or even remove it.

F. Langation (Elongation): These procedures may utilize one or more additional arch-shaped support members. This may involve the use of a proximal (upper) arch-shaped support member, distal (lower) arch-shaped support member (which are support members of persistent fixation), and a third arch-shaped support member, which is implementation at or adjacent the area of the osteotomy. In one treatment methodology, this middle support member may be fixed lower than the osteotomy. Beneficial implementation of this device in elongation of leg fractures with bone defects has been demonstrated. In the treatment of a knee defect, a 0.5 centimeter movement was observed after a seven-day treatment duration. Fixation of inferior site of tibia bone with ankle joint fracture.

Fixation of the inferior site of a tibia bone in patients presenting with ankle-joint fractures requires fixation of both the tibia and ankle joint. In this case, one support member having four K-wires may be used to fix the distal ankle with another support member used to fixed metatarsus bone region. The applied force is transferred from the foot to the support member and from the support member to the support member fixed to the distal part of the leg via the axially-extending rod members. Thus, strong and stable fixation of these kinds of fractures is achieved using this device. Dividing of force in upper side: One of main characteristics of this device is the action of dividing the applied force between two sides of the fracture area. Through extensive testing, it was determined that superior fixation performance could be achieved when the applied force was divided between two sides of the fracture area, in the manner described herein. In this unusual arrangement, both sides of the fracture are placed under persistent pressure, which greatly reduces or eliminates displacing movement of the bone segments opposite of other. In this device one side provides a rigid and persistent fixed point of anchorage with the other side forming a rigid and persistent fixation with the bone structures.

Preferred features of the disclosed device include:
Using the K-wire and also placing the K-wires in one pivot in this device. This feature differs from other devices that use pins in that one pin is equal to roughly 10 K-wires.
Decreasing the risk of neuro vascular damage: K-wire is used in this device and it cross the height of bone in one side to reduce the risk of neuro vascular damage.
Another characteristic of this device is dividing the applied force between two sides during fixation of fractures.
Wide usage of this device in both open and closed infected fractures in both the upper and lower parts of the body.
The device can easily fix the upper side angle in a fractured area.

General Biomechanics of Sadat Fixation Device:
1. Rigidity of arms
2. Number of arms
3. Size/diameter of arms
4. Threaded rods between two arms
5. Length of arm with respect to each other
6. Arm angle when decrease diametrically
7. Distance between soft tissue and arm
   a. Stability of wire factors
8. Cross angle of wires
9. Diameter of wires
10. Centralization of wires longitudinally
11. Minimum three wires at each arm
    a. Intrinsic stability factors
12. Stability of whole apparatus
13. Quality and quantity of soft tissue
14. Tight inner diameter of arm
15. Good reduction General Summary of Features:
1. As this device is generally implemented on only one side of the body, the patient is free to use the other side without encumbrances.
2. Fixation of ankle joint area, deactivation of the ankle joint area is another characteristic of this device.
3. The device is easily removed after treatment or completion period. Generally, no anesthesia is needed as the K-wires are easily removed from the area.
4. In children with open and closed fractures where conservative treatments have failed to provide a positive response, implementation of this device can create firm and persistent fixations producing positive results. In fixation of pediatric fractures using this device, plate fixation using K-wires is primarily used. Also, the weight is less in pediatric applications.
5. K-wire: In general, two K-wire configurations are used in this device, one of small size having diameter of 1.5 millimeters, the other are large-diameter threaded K-wires having a diameter of 2 or 2.5 mm. The small-diameter K-wires are used in the fixation of humorous, ulna, and radius fractures. The larger K-wires are used in fixation of tibia and femur fractures.

Figure 4:
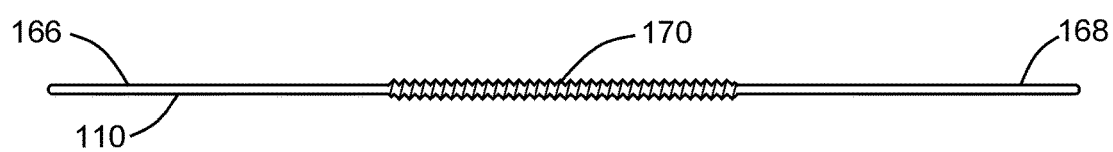
FIG. 4 shows a side view of a bone-fixation wire utilized by the external bone fixator apparatus of FIG. 1, according to an alternate embodiment of the present disclosure.
Figure 5:
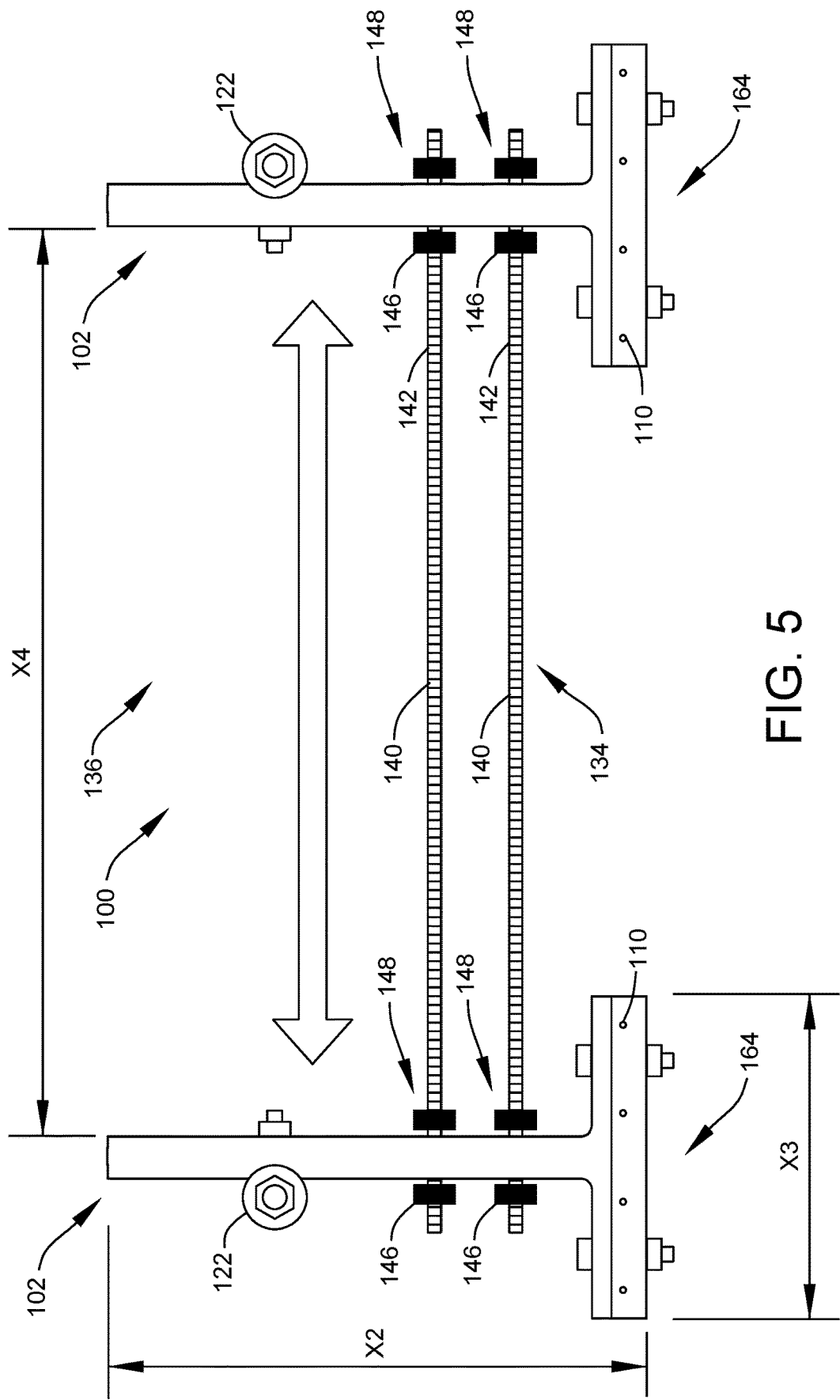
FIG. 5 shows a side view of the external bone fixator apparatus of FIG. 1, according to an alternate embodiment of the present disclosure.
Figure 6:
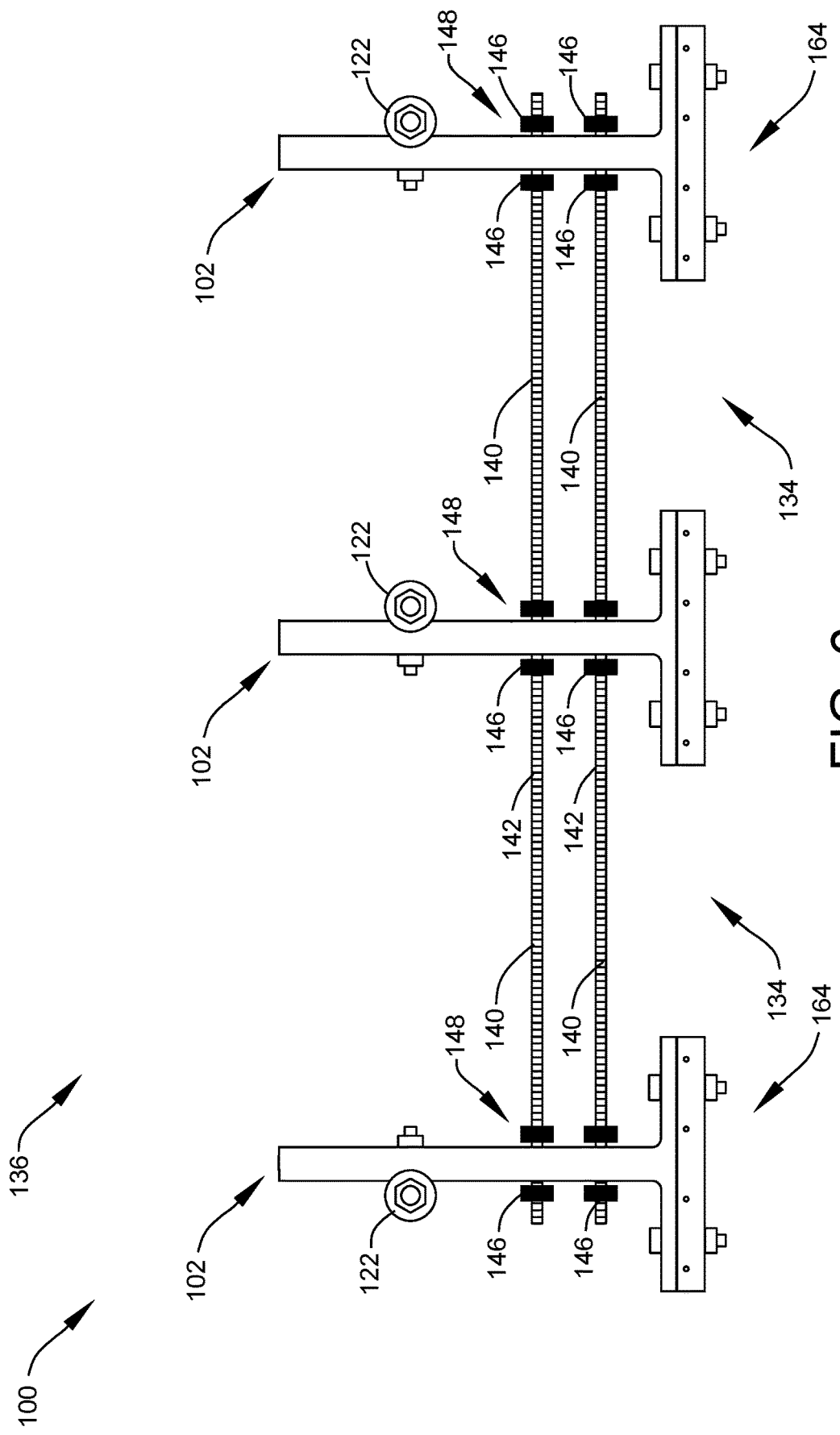
FIG. 6 shows a side view of an alternate arrangement of the external bone fixator apparatus of FIG. 1, according to an alternate embodiment of the present disclosure.

Referring now more specifically to the drawings by numerals of reference, there is shown in FIGS. 1-9, various views of an external bone fixator apparatus 100. FIG. 1 shows an external bone fixator apparatus 100 during an 'in-use' condition 150, according to an embodiment of the present disclosure. As Illustrated, the external bone fixator apparatus 100 may include a plurality of arch-shaped support members 102, as shown. In the depiction of FIG. 1, the external bone fixator apparatus 100 is assembled using two arch-shaped support members 102; however, additional support members may be utilized, as shown in FIG. 6.

Each arch-shaped support member 102 may include a first arm 104 having a first distal end 106 adapted to support a first wire-retainer 108. The first wire-retainer 108 may be configured to firmly retain a first set of bone-fixation wires 110 usable to position a bone part 120 subject to treatment. Each arch-shaped support member 102 may further include a second arm 112 pivotally joined to the first arm 104, as shown. The second arm 112 may include a second distal end 114 supporting a second wire-retainer 116 joined with the second distal end 114. The second wire-retainer 116 may be configured to firmly retain a second set of bone-fixation wires 110 or the opposing ends of the same set of bone-fixation wires 110, as shown.

The first arm 104 and the second arm 112 of the arch-shaped support member 102 defines an open central region 118 adapted to receive a body portion containing the bone part 120 (i.e., an arm, leg, etc.). The open central region 118 may comprise an open side 126 adapted to pass the body portion containing the bone part 120 therethrough, as shown. Each arch-shaped support member 102 may include a distance-of-separation adjuster 122 configured to enable user-selected adjustments to a separation distance X1 (see FIG. 3) between the first wire-retainer 108 and such second wire-retainer 116, and which also defines the width of the open side 126. Manipulation of the distance-of-separation adjuster 122 also allows adjustments to the size of the open area within the open central region 118; thus, the distance between the device and the soft tissue of the limb may be increased or decreased as required.

The distance-of-separation adjuster 122 may include a pivot joint 128 configured to pivotally join the first arm 104 and the second arm 112. In addition, the distance-of-separation adjuster 122 may include a threaded adjustment rod 130 operably connected to a set of rod-receiving blocks 132. In one arrangement of the apparatus, the first arm 104 and the second arm 112 each have one rod-receiving block 132, as shown. The assembly is configured such that rotation of the threaded adjustment rod 130 produces a pivotal adjustment of the first arm 104 and the second arm 112 about the pivot joint 128. This pivotal adjustment enables the above-noted user-selected adjustments to the separation distance X1 between the first wire-retainer 108 and the second wire-retainer 116 of a respective arch-shaped support member 102. Both the width of the open side 126 and tension and compression forces applied to the bone by the bone-fixation wires 110 may be adjusted in this manner.

A plurality of strut-rod assemblies 134 may be provided, as shown. The strut-rod assemblies 134 may be configured to rigidly connect adjacent such arch-shaped support members together to define the depicted fixator frame 136. Each strut-rod assembly 134 may include one or more axially-extending rod members 140 configured to extend between the arch-shaped support members 102. As noted above, each connection point of upper axially-extending rod members are capable of about two centimeters of rotational movement. Thus, the distal and proximal arch-shaped support members 102 can achieve a relative rotational movement of about four centimeters in opposing directions.

According to one embodiment, the external bone fixator apparatus 100 may be arranged as a kit 105. The kit 105 may include a set of instructions 155. The instructions 155 may detail functional relationships in relation to the structure of the external bone fixator apparatus 100 (such that the external bone fixator apparatus 100 can be used, maintained, or the like, in a preferred manner).

Figure 2:
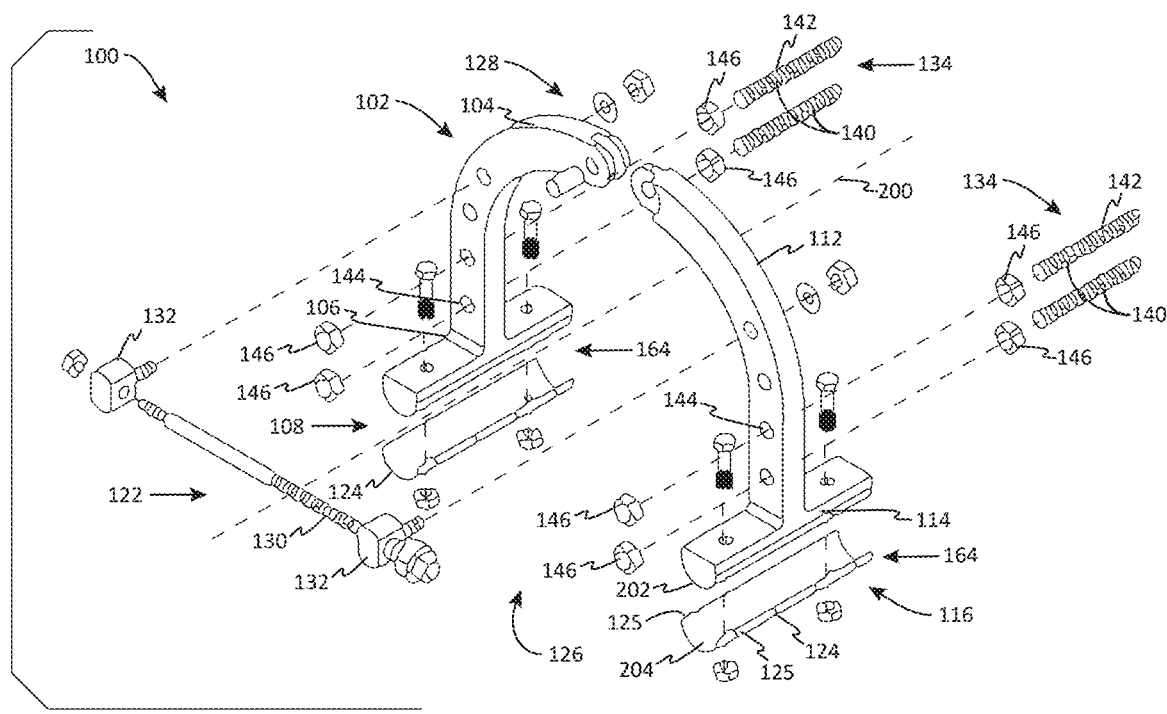
FIG. 2 shows a partial front perspective view of the external bone fixator apparatus of FIG. 1, according to an embodiment of the present disclosure.
Figure 3:
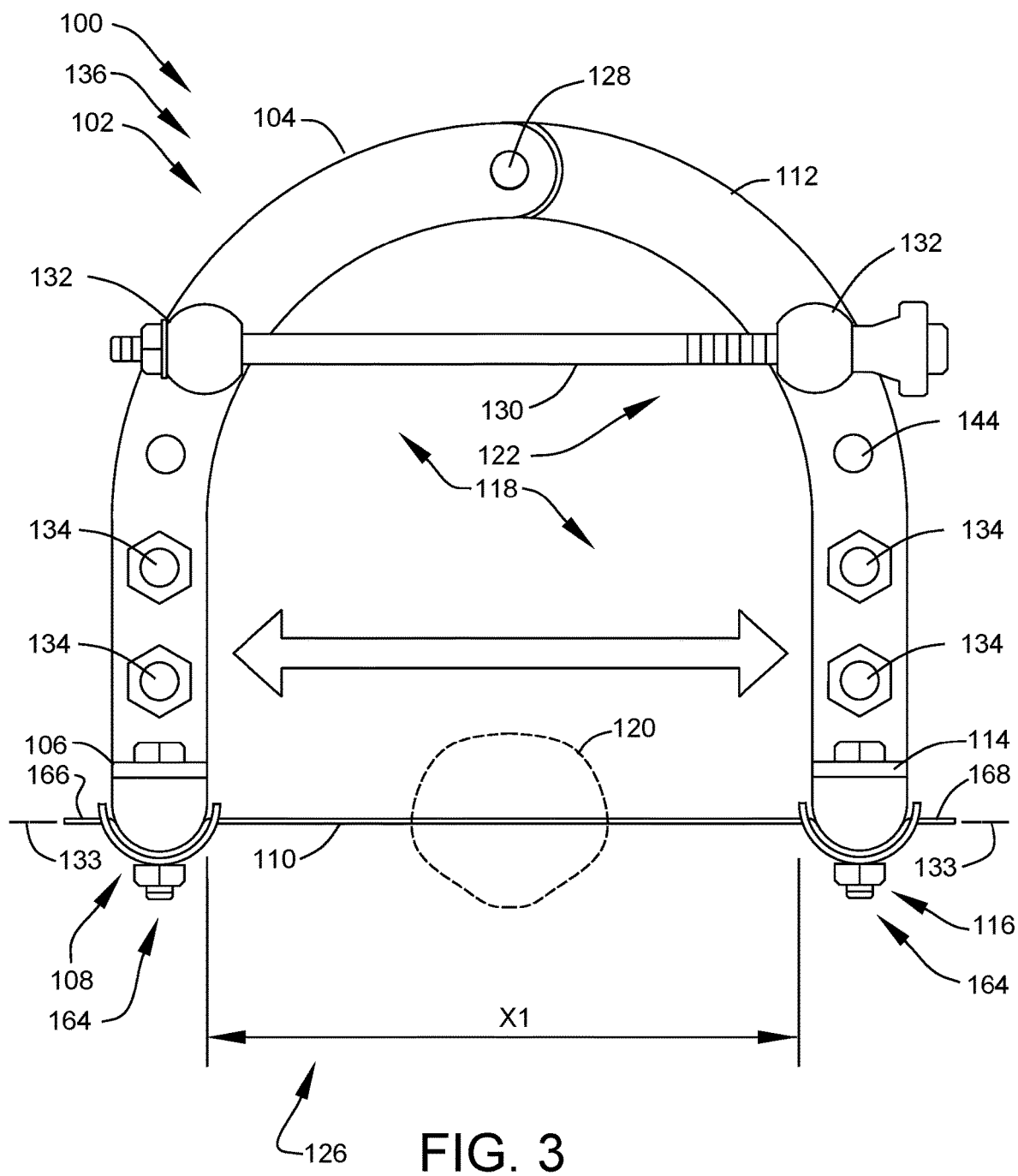
FIG. 3 shows an end view of the external bone fixator apparatus of FIG. 1, according to an embodiment of the present disclosure.

FIG. 2 shows a partial front perspective view of the external bone fixator apparatus 100 of FIG. 1, according to an embodiment of the present disclosure. FIG. 3 shows an end view of the external bone fixator apparatus 100 of FIG. 1, according to an embodiment of the present disclosure. The end view of FIG. 3 illustrates the operational arrangements of the wire-retainers of the external bone fixator apparatus 100. Each of the wire-retainers of the arch-shaped support members 102 may be configured to firmly retain a set of bone-fixation wires 110, as shown. As above, the first wire-retainer 108 may be configured to firmly retain a first set of bone-fixation wires 110 usable to position the bone part 120 subject to treatment. The second wire-retainer 116 may be structured and arranged to enable bone-fixation wires 110 of the second set to include at least one bone-fixation wire 110 of the first set. This is achieved when the ends of the same bone-fixation wires 110 extend from the first wire-retainer 108, through the bone, to the second wire-retainer 116, as shown. More specifically, the geometric configuration of the arch-shaped support member 102 is such that a single plane 133 containing the bone-fixation wires 110 may pass through the first wire retainer 108, the second wire retainer 116, and the bone part 120 of the fracture being treated. As shown, arch-shaped support members 102 may geometrically circumscribe bone-axis 200, along which bone part 120 is to be aligned. First distal end 106 and second distal end 114 may each be T-shaped, and may each have a domed clamping surface 202. Domed clamping surface 202 may be convex, such that the convexity faces away from pivot joint 128. In conjunction, each of first wire retainer 108 and second wire retainer 116 may be characterized by a concavity 204 which corresponds to domed clamping surface 202. In this way, K-wire bone-fixation wires 110 may be clamped between domed clamping surface 202 and concavity 204.

Referring to both FIG. 2 and FIG. 3, with continued reference to FIG. 1, the first wire-retainer 108 and the second wire-retainer 116 are both configured to receive and retain Kirschner-type wires (K-wire bone-fixation wires 110). The first wire-retainer 108 and the second wire-retainer 116 each comprise a clamp 164 to releasably clamp 164 the K-wire bone-fixation wires 110 in place. The clamp 164 may include an arcuate plate 124 that is adjustably bolted to a respective wire retainer, as shown. The arcuate plate 124 may include set apertures 125 through which the bone-fixation wires 110 pass, as shown. In one embodiment of the present disclosure, the first wire-retainer 108 and the second wire-retainer 116 are configured to each retain at least four K-wire bone-fixation wires 110, as shown. The bone-fixation wires 110 may be aligned orthogonally to the arch-shaped support members 102 and wire-retainers. Alternately, the bone-fixation wires 110 may extend through the bone in a non-orthogonal "crossed" wire pattern.

K-wire bone-fixation wires 110 suitable for use in the present device have a first wire end 166 and a second wire end 168 opposite the first wire end 166. The first wire-retainer 108 is configured to firmly retain the first wire end 166. The second wire-retainer 116 is configured to firmly retain the second wire end 168.

FIG. 4 shows a side view of a bone-fixation wire 110 utilized by the external bone fixator apparatus 100 of FIG. 1, according to an alternate embodiment of the present disclosure. The K-wire bone-fixation wires 110 used in conjunction with this device may include a centrally-threaded portion 170 to provide firm mechanical engagement with the bone structure. As noted above, unusual wire configuration creates a resister fixation in the fracture area and assists in controlling lateral movement of the bone during reduction.

As above, the two K-wire configurations used in this device are a small size having diameter of 1.5 millimeters, and a large-diameter threaded K-wires having a diameter of 2 or 2.5 mm. The small-diameter K-wires are used in the fixation of humorous, ulna, and radius fractures. The larger K-wires are used in fixation of tibia and femur fractures.

Referring again to FIG. 1 through FIG. 3, each axially-extending rod member 140 joining the arch-shaped support members 102 is provided with external threads 142, as shown. Furthermore, each of the arch-shaped support members 102 include a set of apertures 144 adapted to slidably receive the threaded portions of the axially-extending rod members 140. Each strut-rod assembly 134 may be secured to the arch-shaped support members 102 using a set of threaded nuts 146 configured to engage the external threads and such arch-shaped support members 102, as shown.

In one embodiment of the present disclosure, each fixator frame 136 utilizes at least four strut-rod assemblies 134, as shown. Each of the arch-shaped support members 102 is configured to receive the axially-extending rod members 140 of the four strut-rod assemblies 134, as shown. Thus, each arch-shaped support member 102 may include four apertures 144 to receive the strut-rod assemblies 134. It should be noted that additional apertures 144 may be provided to accommodate additional strut-rod assemblies 134 or to provide flexibility of placement.

FIG. 5 shows a side view of the external bone fixator apparatus 100 of FIG. 1, according to an embodiment of the present disclosure. The arch-shaped support members 102 may be supplied in a range of sizes, according to the type of treatment being performed. In one embodiment of the present disclosure, the arch-shaped support members 102 may have a height X2 of about 15 centimeters and a width (at the distal wire-retainers) of about 6 centimeters. Alternate embodiments of the apparatus may include larger arch-shaped support members 102 or smaller arch-shaped support members 102, as required.

The arch-shaped support members 102 may be constructed from at least one rigid and durable material. More specifically, the material forming the arch-shaped support members 102 may be selected from the group consisting of platinum, aluminum, steel, plastic, and fiber-reinforced composites.

Each strut-rod assembly 134 may include at least one positional adjuster 148 configured to adjust relative geometrical positions of the adjacent arch-shaped support members 102. In one embodiment of the present disclosure, the threaded nuts 146 located at arch-shaped support members 102 may form the positional adjusters by enabling translational movement of the arch-shaped support members 102 along the axially-extending rod member 140. This is achieved when the threaded nuts 146 are rotated to adjust their positions, and positions of the arch-shaped support members 102, along the rod members. Thus, the distance X4 between the two arch-shaped support members 102 may be increased or decreased, as required.

FIG. 6 shows a side view of an alternate arrangement of the external bone fixator apparatus 100 of FIG. 1, according to an alternate embodiment of the present disclosure. As noted above, some procedures may utilize one or more additional arch-shaped support members 102. This may involve the use of a proximal (upper) arch-shaped support member 102, distal (lower) arch-shaped support member 102 (which are support members of persistent fixation), and a third arch-shaped support member 102, as shown, which may be implementation at or adjacent the area of the osteotomy in an elongation procedure.

Figure 7:
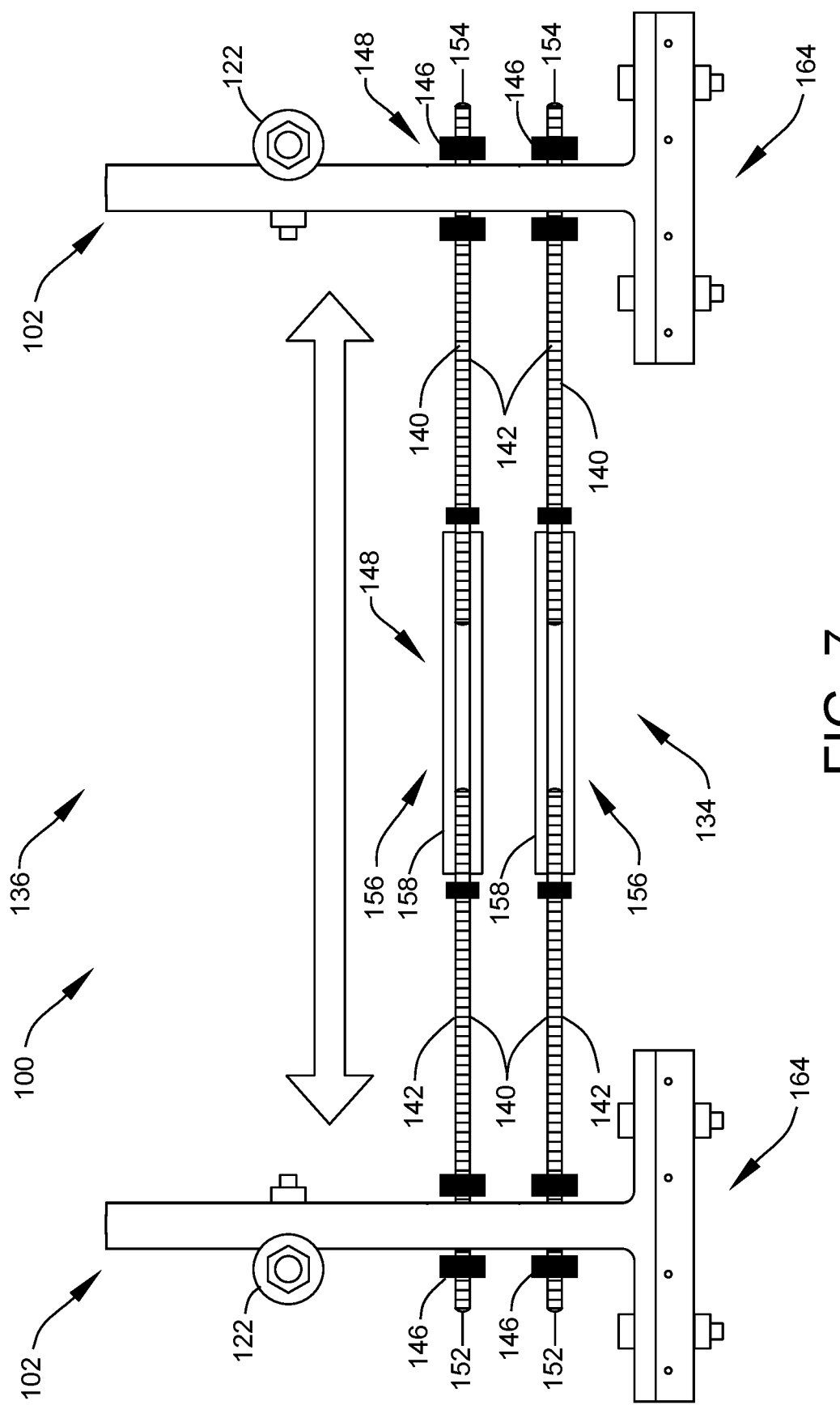
FIG. 7 shows a side view of an alternate arrangement of the external bone fixator apparatus of FIG. 1, according to an alternate embodiment of the present disclosure.

FIG. 7 shows a side view of an alternate arrangement of the external bone fixator apparatus 100 of FIG. 1, according to an alternate embodiment of the present disclosure. As above, the positional adjuster 148 may be configured to adjust relative geometrical positions of such adjacent such arch-shaped support members. In this embodiment, each of the axially-extending rod members 140 are divided to form a first rod segment 152 and a second rod segment 154 independent of the first rod segment 152. In this arrangement, the first rod segment 152 may be engaged with a first arch-shaped support member 102. The second rod segment 154 may be engaged with a second arch-shaped support member 102, as shown. Each of the axially-extending rod members 140 may include an adjustable coupler 156 configured adjustably couple the first rod segment 152 and the second rod segment 154. The adjustable coupler 156 may be supplied as an internally-threaded coupler 158 configured threadably couple the first rod segment 152 and the second rod segment 154 using the external threads 142 of the rods, as shown. The internally-threaded coupler 158 may be arranged to produce translational movement of at least one of the arch-shaped support members 102 when rotated.

Figure 8:
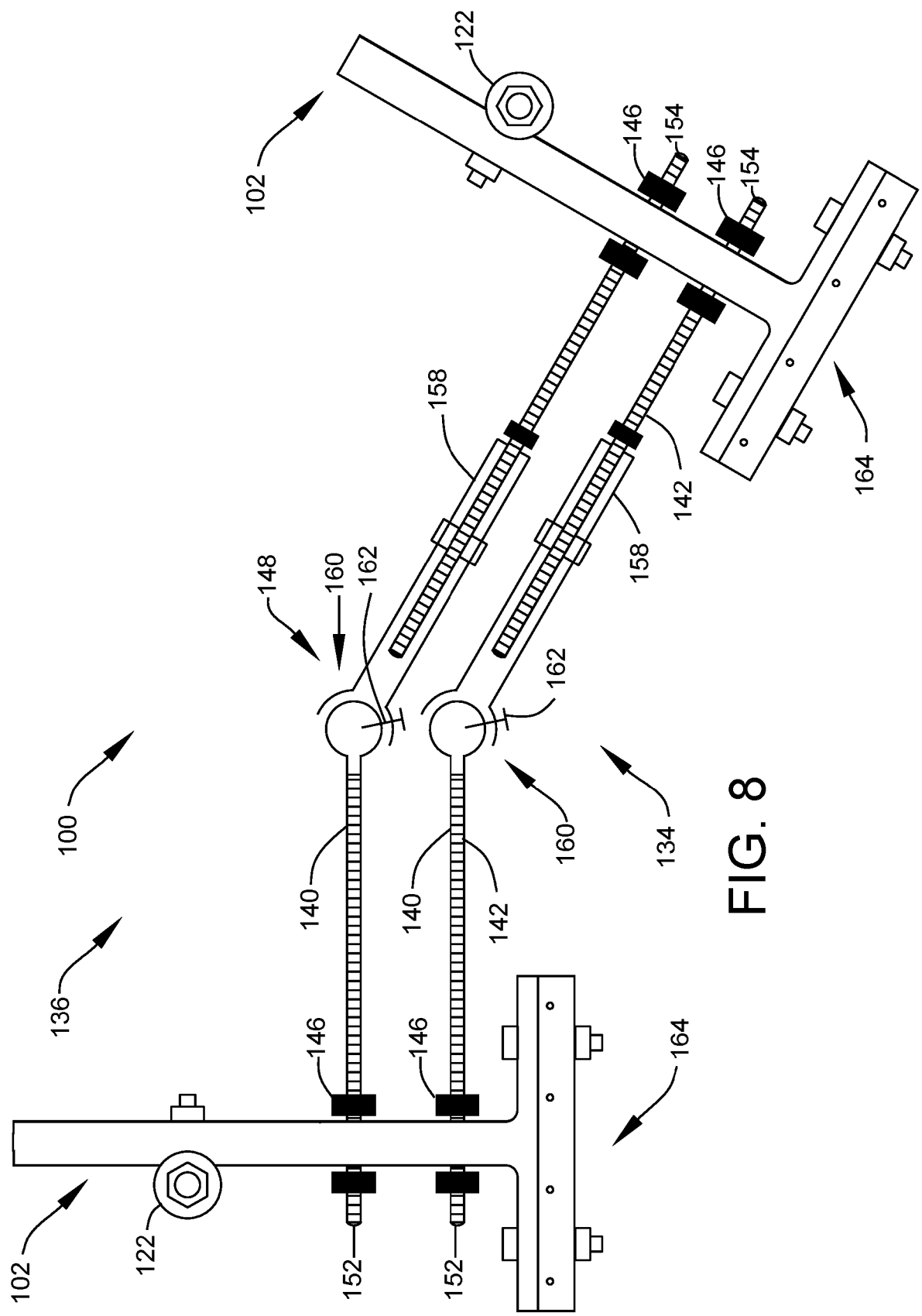
FIG. 8 shows a side view of an alternate arrangement of the external bone fixator apparatus of FIG. 1, according to an alternate embodiment of the present disclosure.

FIG. 8 shows a side view of an alternate arrangement of the external bone fixator apparatus 100 of FIG. 1, according to an alternate embodiment of the present disclosure. As above, the positional adjuster 148 may be configured to adjust relative geometrical positions of such adjacent such arch-shaped support members. In this embodiment, the positional adjuster 148 comprises an articulatable joint 160 configured to enable selected adjustments of an angular relationship between axes of the first rod segment 152 and such second rod segment 154. Additionally, the articulatable joint 160 may include an articulation lock 162 configured to lock a selected angular relationship between such axes of the first rod segment 152 and the second rod segment 154. The articulatable joint 160 may provide, for example, a 10-degree angular adjustment. Upon reading this specification, it should be appreciated that, under appropriate circumstances, considering such issues as user preferences, design preference, structural requirements, marketing preferences, cost, available materials, technological advances, etc., other adjustment arrangements such as, for example, greater or lesser adjustment amounts, etc., may be sufficient.

Moreover, the positional adjuster 148 may also include an internally-threaded coupler 158 configured threadably couple the alternate articulatable joint 160 with either the first rod segment 152 or the second rod segment 154, as shown. In this alternate arrangement, the internally-threaded coupler 158 is structured and arranged to produce translational movement of at least one of the arch-shaped support members 102, more specifically, the arch-shaped support member 102 joined with the rod segment engaged with the internally-threaded coupler 158.

Figure 9:
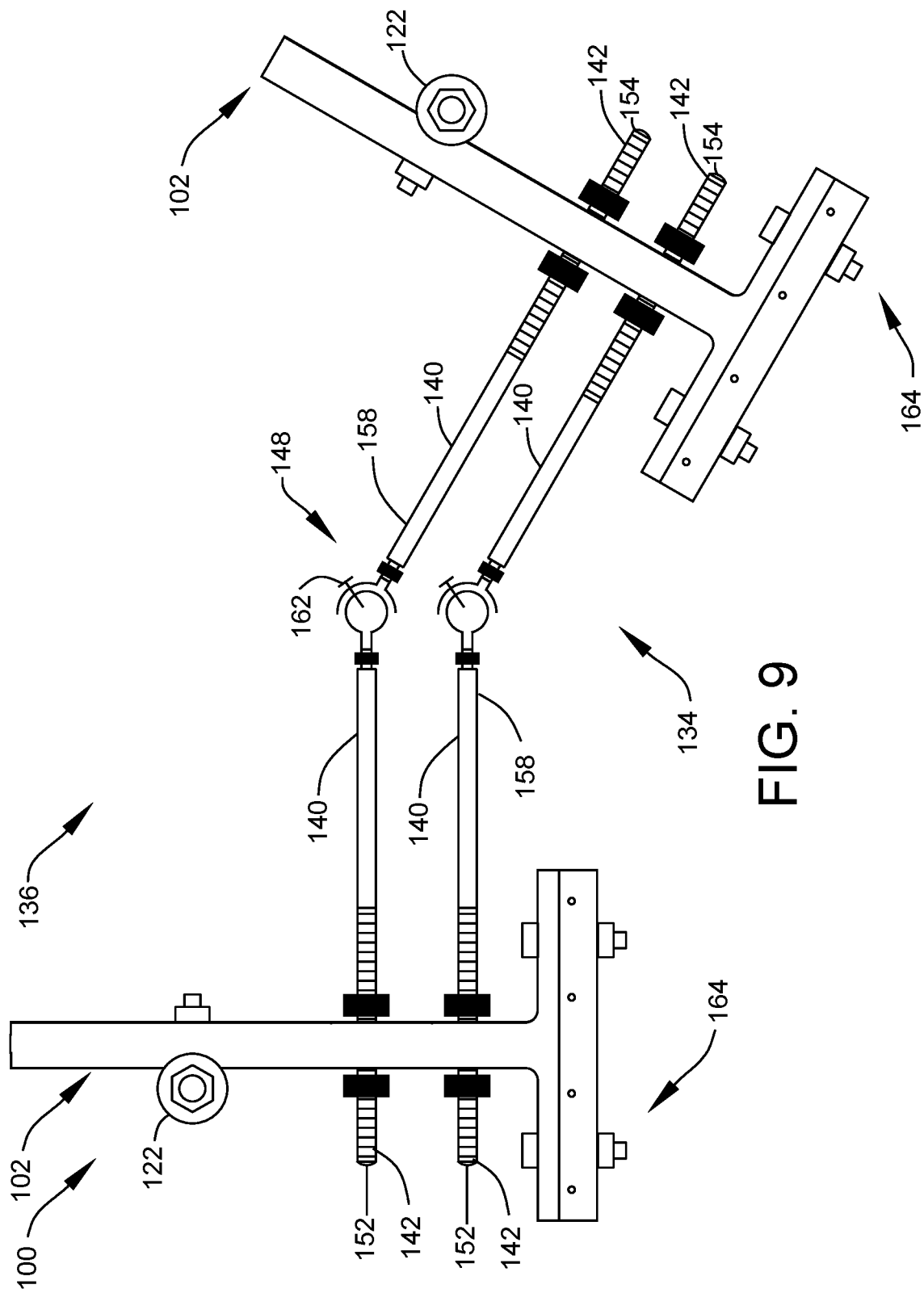
FIG. 9 shows a side view of an alternate arrangement of the external bone fixator apparatus 100 of FIG. 1, according to another embodiment of the present disclosure.

FIG. 9 shows a side view of an alternate arrangement of the external bone fixator apparatus 100 of FIG. 1, according to an alternate embodiment of the present disclosure. As above, the positional adjuster 148 may be configured to adjust relative geometrical positions of such adjacent such arch-shaped support members. In this embodiment, the ends of the first rod segment 152 and the second rod segment 154 include internally-threaded coupler 158 configured threadably couple with externally-threaded portions of an alternate articulatable joint 160, as shown. In this alternate arrangement, the internally-threaded couplers of the rods are structured and arranged to produce translational movement of at least one of the arch-shaped support members 102. It is noted that the articulatable joints 160 may include ball and socket joints, planar joints operating about a single transverse axis, etc. Those with ordinary skill in the art will now appreciate that upon reading this specification and by their understanding the art of mechanically articulated joints, as described herein, methods of implementing such joints will be understood by those knowledgeable in such art.

Figure 10:
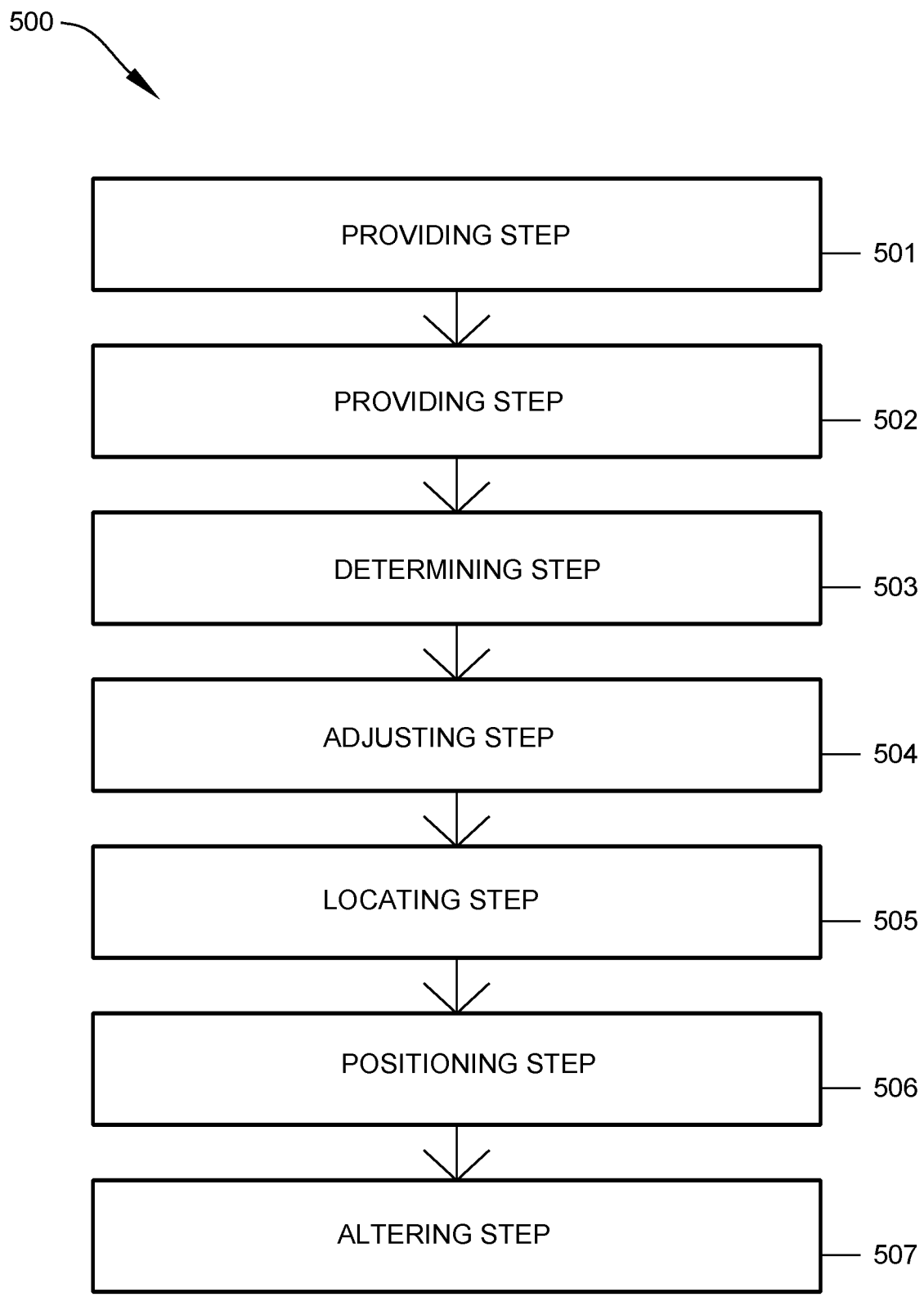
FIG. 10 is a flow diagram illustrating a method of use for an external bone fixator apparatus for use in orthopedic surgery and treatments, according to an embodiment of the present disclosure.

FIG. 10 is a flow diagram illustrating a method 500 of using an external bone fixator apparatus, according to an embodiment of the present disclosure. As illustrated, the method 500 of using an external bone fixator apparatus may include the steps of: step one 501, providing at least two arch-shaped support members, each arch-shaped support member including a first arm having a first distal end thereof, a first wire retainer joined with the first distal end, the first wire-retainer configured to firmly retain a first set of bone-fixation wires usable to position a bone part, a second arm pivotally joined to the first arm, the second arm having a second distal end thereof, a second wire retainer joined with the second distal end, the second wire-retainer configured to firmly retain a second set of bone-fixation wires, the second wire-retainer structured and arranged to enable bone-fixation wires of the second set to include at least one bone-fixation wire of the first set, and a distance-of-separation adjuster configured to enable user-selected adjustments to a separation distance between the first wire retainer and the second wire retainer of a respective arch-shaped support member; step two 502, providing a plurality of strut-rod assemblies configured to rigidly connect adjacent the arch-shaped support members together to define a fixator frame, each strut-rod assembly including axially-extending rod members configured to extend between the arch-shaped support members, and a positional adjuster configured to adjust relative geometrical positions of the adjacent arch-shaped support members; step three 503, determining a distance of separation between the first wire retainer and the second wire retainer of each arch-shaped support member required to accommodate a body portion containing the bone part; step four 504, adjusting the first wire retainer and the second wire retainer of each arch-shaped support member to the required distance of separation; step five 505, locating the arch-shaped support members adjacent the bone parts of a fracture such that a plane extending between the first wire retainer and the second wire retainer of each arch-shaped support member passes through a respective bone part of the fracture; step six 506, positioning the bone parts of the fracture by engaging the bone-fixation wires within the first wire retainers, the second wire retainers and the respective bone parts.

Even further, method 500 further comprising the step seven 507 of altering the positions of the bone parts by adjusting the relative geometrical positions of the adjacent arch-shaped support members using the positional adjuster. It should be noted that step 507 is an optional step and may not be implemented in all cases. Optional steps of method of use 500 are illustrated using dotted lines in FIG. 10 so as to distinguish them from the other steps of method 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for an external bone fixator apparatus 100 (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An external bone fixator apparatus for use in orthopedic surgery and treatments, said apparatus comprising:
   a plurality of arch-shaped support members, said plurality of arch-shaped support members configured to circumscribe a bone-axis, each said arch-shaped support member including
      a first arm having a first distal end thereof, said first distal end being T-shaped,
      a first wire retainer joined with said first distal end, said first wire-retainer configured to firmly retain a first set of bone-fixation wires usable to position a bone part, said first wire retainer configured to extend parallel with the bone-axis, said first wire retainer having at least three parallel bores, said at least three parallel bores of the first wire retainer configured to extend perpendicular to the bone-axis,
      a second arm pivotally joined to the first arm at a pivot joint, said second arm having a second distal end thereof, said second distal end being T-shaped,
      a second wire retainer joined with said second distal end, said second wire-retainer configured to firmly retain a second set of bone-fixation wires, said second wire-retainer structured and arranged to enable bone-fixation wires of the second set to include at least one bone-fixation wire of the first set, said second wire retainer configured to extend parallel with the bone-axis, said second wire retainer having at least three parallel bores, said at least three parallel bores of the second wire retainer configured to extend perpendicular to the bone-axis, and
      a distance-of-separation adjuster configured to enable user-selected adjustments to a separation distance between said first wire retainer and said second wire retainer of a respective said arch-shaped support member by altering angulation between said first arm and said second arm;
   wherein each of said first distal end and second distal end comprise a domed clamping surface, said domed clamping surface being convex distally to said pivot joint,
   wherein said first wire retainer and said second wire retainer each comprise a concavity, said concavity being shaped and dimensioned to mate with said domed clamping surface; and
   a plurality of strut-rod assemblies configured to rigidly connect adjacent said arch-shaped support members together to define a fixator frame, each said strut-rod assembly including
      axially-extending rod members configured to extend between said arch-shaped support members, and
      a positional adjuster configured to adjust relative geometrical positions of such adjacent said arch-shaped support members.

2. The apparatus of claim 1, further comprising Kirschner-type wires;
   wherein the first wire retainer and second wire retainer are configured to receive and retain said Kirschner-type wires by clamping said Kirschner-type wires between said domed clamping surface and said concavity.

3. The apparatus of claim 2 wherein said first wire retainer and said second wire retainer are configured to retain at least four of such Kirschner-type wires.

4. The apparatus of claim 2 wherein:
   such Kirschner-type wires comprise a first wire end and a second wire end opposite the first wire end;
   said first wire-retainer is configured to firmly retain such first wire end; and
   said second wire-retainer is configured to firmly retain such second wire end.

5. The apparatus of claim 1, wherein said distance-of-separation adjuster comprises:
   said pivot joint configured to pivotally join said first arm and said second arm; and
   threaded adjustment rod connecting said first arm and said second arm;
   wherein said first arm and said second arm each include a rod-receiving block designed to receive the threaded rod;
   wherein rotation of said threaded adjustment rod produces pivotal adjustment of said first arm and said second arm about said pivot joint; and
   wherein such pivotal adjustment of said first arm and said second arm about said pivot joint enables such user-selected adjustments to said separation distance between the first wire retainer and second wire retainer of a respective said arch-shaped support member.

6. The apparatus of claim 1 wherein each said axially-extending rod member comprises external threads.

7. The apparatus of claim 6 wherein:
- each arch-shaped support member comprises at least one aperture adapted to slidably receive said axially-extending rod member comprising said external threads; and
- each said strut-rod assembly further comprises a set of threaded nuts configured to engage said external threads and said arch-shaped support member.

8. The apparatus of claim 7 wherein said threaded nuts are structured and arranged to produce translational movement of said arch-shaped support member along said axially-extending rod member when said threaded nuts are rotated.

9. The apparatus of claim 1 wherein each said arch-shaped support member is configured to receive at least four said axially-extending rod members.

10. The apparatus of claim 1 wherein:
- said first arm and said second arm of said arch-shaped support member defines an open central region adapted to receive a body portion containing the bone part;
- said open central region comprises an open side adapted to pass the body portion therethrough.

11. The apparatus of claim 1 wherein the arch-shaped support members are constructed from at least one material selected from the group consisting of platinum, aluminum, steel, plastic, and fiber-reinforced composites.

* * * * *